United States Patent [19]

Gaydos

[11] 4,317,473

[45] Mar. 2, 1982

[54] FLUID FLOW CONTROL ASSEMBLY

[75] Inventor: Joseph A. Gaydos, Clifton, N.J.

[73] Assignee: Becton, Dickinson and Company, Paramus, N.J.

[21] Appl. No.: 108,955

[22] Filed: Dec. 31, 1979

[51] Int. Cl.[3] ............................................. F15D 1/14
[52] U.S. Cl. ........................................ 138/45; 138/46;
128/214 C; 251/206; 222/420; 222/485
[58] Field of Search ......................... 222/71, 420–422,
222/485, 488, 547, 564, 548, 554; 251/206–209,
125; 128/214 R, 214 C; 138/43, 45, 46;
119/72.5; 239/542

[56] References Cited

U.S. PATENT DOCUMENTS

| 784,228 | 3/1905 | Richwood | 251/206 |
|---|---|---|---|
| 3,233,457 | 2/1966 | Martinez | 251/206 |
| 3,323,774 | 6/1967 | Wilson | 128/214 C |
| 3,785,378 | 1/1974 | Stewart | 251/207 X |
| 3,998,227 | 12/1976 | Holbrook et al. | 251/207 X |
| 4,079,737 | 3/1978 | Miller | 251/207 X |
| 4,096,879 | 6/1978 | Serur et al. | 138/45 X |
| 4,176,683 | 12/1979 | Leibinsohn | 138/43 X |
| 4,177,947 | 12/1979 | Menzel | 251/209 X |

Primary Examiner—Charles A. Marmor

[57] ABSTRACT

A flow control assembly, particularly for intravenous usage, is comprised of a fluid receiving member having a fluid channel and a fluid conduit in fluid flow communication with a source of intravenous fluid; a fluid dispensing member preferably including a drip chamber for connecting a conduit thereto; and fluid flow control member positioned between the fluid receiving member and the fluid dispensing member and having a plurality of flow channels of predetermined cross-section thereby forming with the fluid dispensing member calibrated flow passageways to the drip chamber whereby rotation of the fluid dispensing member with respect to the fluid receiving member selectively orients the fluid channel of the fluid receiving member to one of the calibrated flow passageways thereby to establish a predetermined fluid flow rate from the source of the intravenous fluid to the recipient thereof.

6 Claims, 4 Drawing Figures

U.S. Patent     Mar. 2, 1982     4,317,473
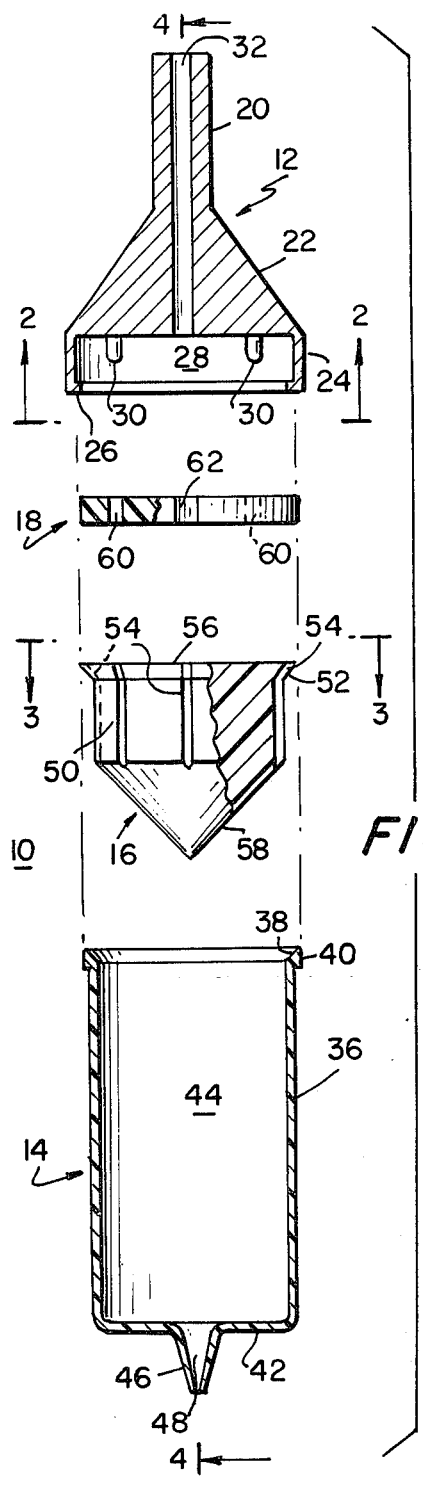
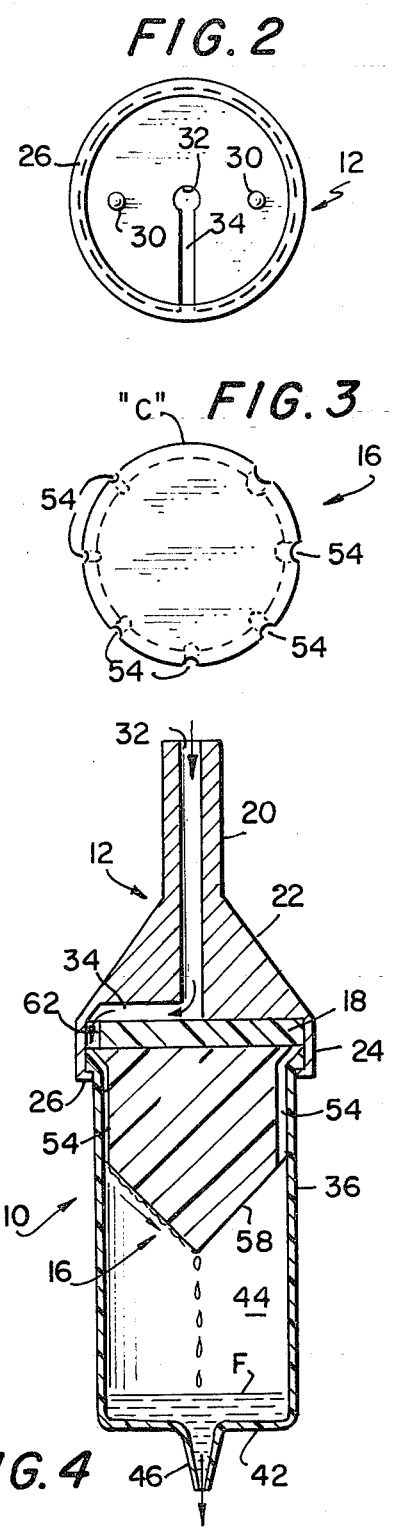

FLUID FLOW CONTROL ASSEMBLY

This invention relates to fluid flow control assemblies, and more particularly to a novel fluid flow control assembly for selecting and controlling at various flow rates the gravity flow of fluid therethrough in a facile and accurate manner.

BACKGROUND OF THE INVENTION

At present, intravenous assemblies for controlling the flow of a intravenous solution to a patient are generally of the gravity feed type including a drip chamber to which the intravenous fluid is passed from a supply container via a flexible tube under the control of tube clamping assembly adjusted through a threaded arrangement and from which drip chamber the fluid is withdrawn and passed to the recipient. The flow rate of such gravity type intravenous assemblies is determined by visual observation of the rate of droplet release in the drip chamber per unit time, and thus such assemblies suffer from the inherent inability to accurately control the rate of flow of intravenous fluid at predictable flow control levels, other than by such visual observation. Such prior art assemblies are accessible to the patient and may be readily changed by the patient with the attendant dangers of under or over dosages from prescribed dosage requirements.

OBJECTS OF THE INVENTION

An object of the present invention is to provide a novel fluid flow control assembly which permits of more accurate settings of fluid flow rates.

Another object of the present invention is to provide a novel intravenous fluid flow control assembly.

Yet another object of the present invention is to provide a novel intravenous fluid flow control assembly which reduces the likelihood of patient tampering to alter fluid flow rate settings.

Still another object of the present invention is to provide a novel intravenous fluid flow control assembly comprised of rigid components which may be readily assembled.

A further object of the present invention is to provide a novel intravenous fluid flow control assembly which may be repeatedly reused with like solutions.

Yet still another object of the present invention is to provide a novel intravenous fluid flow control assembly obviating the necessity for droplet count per unit time to establish a desired fluid flow setting.

SUMMARY OF THE INVENTION

These and other objects of the present invention are achieved by a fluid flow control assembly comprised of a fluid receiving member having a fluid channel and a fluid conduit in fluid flow communication with a source of intravenous fluid; a fluid dispensing member preferably including a drip chamber and having a conduit member for connecting a conduit thereto; and a fluid flow control member positioned between the fluid receiving member and the fluid dispensing member and having a plurality of flow channels of predetermined cross-section thereby forming with the fluid dispensing member calibrated flow passageways to the drip chamber whereby rotation of the fluid dispensing member with respect to the fluid receiving member selectively orients the fluid channel of the fluid receiving member to one of the calibrated flow passageways thereby to establish a predetermined rate of flow of fluid from the source of intravenous fluid to the recipient thereof. Generally, a gasket is required between the fluid receiving member and fluid flow control member as a result of the inability of the materials of construction to provide for fluid flow integrity.

BRIEF DESCRIPTION OF THE DRAWINGS

Understanding of the present invention will be facilitated by referring to the following detailed description when taken in conjunction with the accompanying drawings in which:

FIG. 1 is an exploded view, partially in section of the fluid flow control assembly of the present invention illustrating the major components thereof;

FIG. 2 is a bottom view of the fluid receiving member;

FIG. 3 is a top view of the fluid flow control member; and

FIG. 4 is an elevational view, in section, of the fluid flow control assembly of the present invention taken along the lines 4—4 of FIG. 1.

DETAILED DESCRIPTION OF THE INVENTION

Referring now to FIG. 1, there is illustrated the novel fluid flow control assembly of the present invention, generally indicated as 10, and comprised of a fluid receiving member, a fluid dispensing member, a fluid flow control member, and a gasket member generally indicated as 12, 14, 16 and 18, respectively. The fluid receiving member 12 is formed of a cylindrically-shaped upper portion 20 dimensioned to be received in a container of intravenous fluid (not shown) and extending to an outwardly and downwardly extending conically-shaped intermediate portion 22 terminating in a cylindrical-shaped bottom wall 24 formed with an inwardly extending ledge 26 generally defining a chamber 28. Stud members 30 are formed on the intermediate portion 22 extending downwardly into the chamber 28. Extending through the top and intermediate portions 20 and 22, there is provided a centrally disposed fluid passageway 32 in fluid communication with a laterally extending channel 34 formed in the intermediate member 22, referring also to FIG. 2.

The fluid dispensing member 14 is formed of a cylindrically-shaped side wall 36 having a conically-shaped flange surface 38 formed on extending flange member 40 and enclosed by a bottom wall 42 thereby defining a drip chamber 44. The bottom wall 42 is provided with a downwardly extending connecting member 46 having an orifice 48 formed therein.

The fluid flow control member 16 is formed of a cylindrically-shaped side 50 having an outwardly extending flange portion 52 and formed with a plurality of longitudinally extending conduits or channels 54, a top portion 56 and a conically-shaped bottom portion 58, also referring to FIG. 3, it being understood that the fluid flow control member 16 may be of hollow construction, although for accurate calibration, solid construction is believed to be more desirable. The conduits or channels 54 are formed of varying cross-sectional areas to thereby form passageways of varying fluid flow rates with the inner surface of the side wall 36 of the fluid dispensing member 14.

The gasket member 18 is disc-shaped and is formed of a suitable gasket material, such as neoprene or the like. The gasket member 18 is dimensioned to closely fit within the chamber 28 of the fluid flow receiving member 12 and is formed with two orifices 60 coincident with the stud member 30 thereof. A trough 62 is formed about a peripheral portion of the gasket member 18.

Referring now FIG. 4, there is illustrated the fluid flow control assembly of the present invention with the cylindrically-shaped gasket member 18 positioned within the chamber 28 of the fluid flow receiving member 12 with the studs 30 being disposed within the orifices 60 of the gasket 18 thereby to align the trough 62 with the channel 34 of the fluid receiving member 12. The fluid dispensing member 14 including fluid flow control member 16 disposed therein is positioned within the chamber 28 such that the inwardly extending ledge 26 of the wall 24 of the fluid receiving member 12 engages in fluid tight relationship the bottom portion of the flange member 40 of the fluid dispensing member 14.

In operation, the top portion 20 of the fluid receiving member 12 is connected to a source of fluid, and in particular, an intravenous fluid, such as by insertion into a container of intravenous fluid (not shown). The initial juxtaposition between the channel 34 of the fluid receiving member 12 and trough 62 of the gasket 18 with respect to the fluid flow control member 16 generally corresponds to the point indicated as "C" on the fluid flow control member 16 whereby no fluid may pass through the fluid flow control assembly 10, although being introduced into the fluid receiving member 12. The outlet connecting member 46 of the fluid dispensing member 14 is attached to a flexible conduit or tubing (not shown) leading to the recipient of the fluid. Thereupon, the fluid dispensing member 14 including the fluid flow control member 16 is caused to be rotated with respect to the fluid receiving member 12 and gasket 18 to align the channel 34 and trough 62, respectively, with a preselect channel of the fluid flow control member 16 to permit liquid at a corresponding rate of flow (depending on the liquid head) to flow through such preselect channel 54 and along the bottom 58 thereby to form droplets which fall through the drip chamber 44 and form a pool of fluid (F). The fluid in the pool of liquid in the lower portion of the drip chamber 44 flows to the recipient via the orifice 48 of the connecting member 46 and flexible tubing (not shown).

While not illustrated on the drawing, an appropriately embossed index, such as an arrow (not shown), may be formed on the outer surface of the bottom portion 24 of the fluid receiving member 12 to correpond to the channel 34 to permit for visual and facile alignment thereof with a preselect channel 54 of the fluid flow control member 16. Additionally, the outer surface of the fluid flow control member 16 may be aseptically marked to indicate the calibrated flow rate for each channel 54, it being understood that the fluid dispensing member is transparent. Alternately, the fluid receiving member 14 and the fluid flow control member may be fabricated with positioning means such that there is select alignment therebetween thereby permitting desired marking on the outer surface of the wall 36 of the flow receiving member 14. It will be further understood by one skilled in the art that a series of fluid flow control assemblies according to the present invention may be manufactured with flow rate capabilities of the channels 54 dependent on the viscosity (at any given temperature range) of the liquid being metered through the assembly.

The components of the fluid flow control assembly of the present invention are conveniently fabricatd from commercial available thermoplastic or thermosetting resins for one-use application, although it will be appreciated by one skilled in the art that for non-aseptic uses, the fluid flow control assembly may be used a plurality of times before disposal or before disassembly and cleaning for subsequent re-assembly and re-use. Additionally, while the fluid flow control assembly of the present invention has been described with a drip chamber, it will be understood by one skilled in the art that the inventive contributive hereof obviates the necessity of such a drip chamber, although it is belieived to be preferably included due to long standing usage of intravenous devices having drip chambers.

While the invention has been described in connection with an exemplary embodiment thereof, it will be understood that many modifications will be apparent to those of ordinary skill in the art and that this application is intended to cover any adaptations or variations thereof. Therefore, it is manifestly intended that this invention be only limited by the claims and the equivalents thereof.

What is claimed:

1. A fluid flow control assembly for the controlled metering of the flow of fluid between a fluid inlet and a fluid outlet thereof, which comprises:
    a fluid receiving member having a fluid inlet and fluid passageway means in fluid flow communication with said fluid inlet; and
    a fluid dispensing member having a fluid outlet and including a plurality of calibrated fluid flow passageways and a fluid chamber, said fluid dispensing member being rotatably mounted to said fluid receiving member, said fluid dispensing member being formed with a cylindrically-shaped inner side wall in which is positioned a fluid control member of cylindrical shape and having a plurality of varying sized channels formed transverse thereof thereby forming with said inner surface of said sidewall of said fluid dispensing member said plurality of calibrated fluid flow passageways, wherein said cylindrically-shaped fluid control member is formed with a conically shaped bottom portion to form a site for droplet formation of said fluid, whereby each of said calibrated fluid flow passageways is selectively positionable with respect to said fluid passageway means of said fluid receiving member thereby to meter in a predetermined manner the flow of fluid through said assembly to said fluid outlet.

2. The fluid flow control assembly as defined in claim 1 wherein said fluid receiving member is formed with a chamber in which said fluid dispensing member is disposed in fluid tight relationship.

3. The fluid flow control assembly as defined in claim 1 wherein a gasket is fixedly disposed with respect to said fluid receiving member in a chamber between said fluid receiving member and said fluid dispensing member.

4. The fluid flow control assembly as defined in claim 3 wherein said fluid receiving member is formed with stud members extending into said chamber and cooperating with orifices in said gasket.

5. The fluid flow control assembly as defined in claim 4 wherein said gasket is formed with a trough about the peripheral portions thereof in fluid flow relationship with said passageway means.

6. The fluid flow control assembly as defined in claim 1 wherein said fluid chamber is sized to permit observation of the rate of droplet formation per unit time.

* * * * *